United States Patent [19]

Akiyama et al.

[11] 4,410,747
[45] Oct. 18, 1983

[54] PROCESS FOR PRODUCING 1,2-DICHLOROETHANE

[75] Inventors: Tsunekazu Akiyama, Kurashiki; Tetsuaki Kihara, Yokohama; Kazunaga Komizo; Hiroshi Kameo, both of Kurashiki, all of Japan

[73] Assignee: Ryo-nichi Company Ltd., Tokyo, Japan

[21] Appl. No.: 276,351

[22] PCT Filed: Dec. 26, 1980

[86] PCT No.: PCT/JP80/00330
§ 371 Date: Jun. 11, 1981
§ 102(e) Date: Jun. 11, 1981

[87] PCT Pub. No.: WO82/02197
PCT Pub. Date: Jul. 8, 1982

[51] Int. Cl.³ .................................. C07C 17/02
[52] U.S. Cl. .................................. 570/247
[58] Field of Search .................................. 570/247

[56] References Cited

U.S. PATENT DOCUMENTS

| 2,929,852 | 3/1960 | Benedict | 570/246 |
| 3,839,475 | 10/1974 | Kurtz et al. | 570/247 |
| 3,911,036 | 10/1975 | DiFiore et al. | 570/247 |
| 3,968,179 | 7/1976 | Strini et al. | 570/247 |

FOREIGN PATENT DOCUMENTS 49-163 1/1974 Japan.
56-7729 1/1981 Japan.

Primary Examiner—Charles F. Warren
Assistant Examiner—Joseph A. Boska
Attorney, Agent, or Firm—Oblon, Fisher, Spivak, McClelland & Maier

[57] ABSTRACT

In the technology for producing 1,2-dichloroethane by reacting ethylene with chlorine by a liquid phase reaction at 65° to 160° C. in 1,2-dichloroethane containing a metal chloride catalyst, there is a disadvantage of a side reaction for producing 1,1,2-trichloroethane etc. at a large ratio to cause lower yield of 1,2-dichloroethane. The present invention is to overcome the disadvantage and to produce 1,2-dichloroethane in high yield by reducing the side reaction by incorporating at least one of aromatic compounds selected from the group consisting of benzene type hydrocarbons having the formula

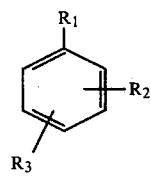

wherein $R_1$, $R_2$ and $R_3$ respectively represent hydrogen atom, $C_1$-$C_5$ alkyl group and chlorinated derivatives thereof as a side reaction inhibitor at a ratio of at least 0.001 wt. % in the reaction medium.

6 Claims, 1 Drawing Figure

PROCESS FOR PRODUCING 1,2-DICHLOROETHANE

FIELD OF TECHNOLOGY

The present invention relates to an improvement of a process for producing 1,2-dichloroethane by a reaction of ethylene with chlorine in a reaction medium containing 1,2-dichloroethane as a main component in a liquid phase at high temperature. More particularly, it relates to a process for producing 1,2-dichloroethane in an industrial effective operation under reducing a side reaction for producing 1,1,2-trichloroethane by a high temperature reaction.

BACKGROUND OF TECHNOLOGY

The high temperature process for producing 1,2-dichloroethane by a liquid phase reaction of ethylene with chlorine at a temperature of 65° to 160° C. in the presence of a metal chloride catalyst in a reaction medium containing 1,2-dichloroethane as a main component has been known in U.S. Pat. No. 2,929,852, U.S. Pat. No. 3,839,475 and British Pat. No. 1,422,303. In accordance with such high temperature process, 1,2-dichloroethane as the reaction product can be obtained in a form of vapor. In such process, the reaction zone can be effectively cooled by the latent heat resulted in the evaporation of 1,2-dichloroethane, whereby a special means for cooling the reaction zone can be advantageously eliminated. Moreover, a heat source for rectification of the product can be saved by feeding the vaporized 1,2-dichloroethane into a rectification tower for purification of 1,2-dichloroethane as a vapor. Both effects are attained.

Recently, such high temperature process has been considered to be important in view of energy saving. Such high temperature process has said advantages, however, has a fundamental disadvantage that the side reaction for producing 1,1,2-trichloroethane is significant at a reaction temperature of 60° C. or higher especially higher than a boiling point of 1,2-dichloroethane as the reaction medium (83° C.) to be lower selectivity to 1,2-dichloroethane as the object product and to be lower yield. Heretofore, a process for overcoming such disadvantages in the high temperature process has been also proposed. For example, British Pat. No. 1,186,742 discloses a process for reducing a production of 1,1,2-trichloroethane by adding only a small amount of oxygen to the reaction mixture by using oxygen as a side reaction inhibitor. The process, imparts the effect for reducing the production of the by-product, however, it has a disadvantage that the unreacted ethylene and oxygen are remained in an uncondensed gas separated from a condensed liquid in a condensation and liquefaction of the resulting 1,2-dichloroethane distilled from a tower top and an explosive mixture is formed by the unreacted ethylene and oxygen.

It is necessary to consider a treatment for preventing the trouble.

In U.S. Pat. No. 3,911,036, a two step reaction process is employed. The first step, imparts a conversion of about 17% at high temperature and the second step imparts a remained conversion at low temperature to reduce the production of the by-product. The two step reaction process has a fatal disadvantage of causing a complication of the process.

SUMMARY OF THE INVENTION

The inventors have studied various liquid phase reactions of ethylene and chlorine especially, reductions of the side reaction for producing 1,1,2-trichloroethane in high temperature liquid phase reaction. As a result, it has been found that the object is attained in the presence of a specific aromatic compound as a side reaction inhibitor at more than a specific ratio in the liquid phase reaction zone. The present invention has been attained by the finding.

That is, the present invention is to provide a process for producing 1,2-dichloroethane by reacting ethylene with chlorine at a reaction temperature of 65° to 160° C. by a liquid phase reaction in a reaction medium containing 1,2-dichloroethane as a main component in the presence of a metal chloride catalyst which comprises incorporating at least one of aromatic compounds selected from the group consisting of benzene type hydrocarbons having the formula

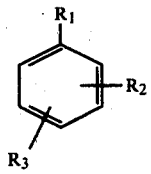

wherein $R_1$, $R_2$ and $R_3$ respectively represent hydrogen atom or a $C_1$-$C_5$ alkyl group; and chlorinated derivatives thereof as a side reaction inhibitor in the liquid phase of the reaction zone at a ratio of at least 0.001 wt.% based on the liquid phase.

The present invention is usually attained by a continuous reaction performed by continuously feeding ethylene and chlorine at 65° to 160° C. in the reaction medium of 1,2-dichloroethane containing effective amounts of the metal chloride catalyst and the side reaction inhibitor in a reactor. In the present invention, the reaction medium (i.e. the resulting 1,2-dichloroethane) in at least the upper liquid layer of the reaction medium is vaporized by a reaction heat caused by the reaction of ethylene and chlorine. The reaction medium in the starting material feeding zone can be maintained in boiling or at a temperature of lower than the boiling point in the condition. The latter is preferable because a clogging of a starting material feeding port caused by an adhesion of the metal chloride catalyst can be prevented. The cooling of the reaction medium in the starting material feeding zone can be easily performed by cooling slightly the bottom of the reactor or by discharging the reaction medium from near the surface of the solution and recycling it to the bottom of the reactor in a loop form.

In the present invention, each rate of ethylene or chlorine fed into the reactor is usually in a range of 100 to 10,000 m/hr. preferably 500 to 5,000 m/hr. A molar ratio of ethylene to chlorine is usually in a range of 0.9 to 1.3 preferably 1.00 to 1.10 as gas superficial velocity. In usual, it is preferable to react them in excess of ethylene. In such case, a conversion of chlorine is almost 100%. It is possible to react them in excess of chlorine. In such case, a conversion of ethylene is almost 100%.

In the present invention, a pressure in the reactor is usually in a range of a reduced pressure to 20 kg/cm²G preferably the atmospheric pressure to 5 kg/cm²G. A reaction temperature is a temperature for boiling the upper liquid surface layer of the reaction medium under the pressure in the reactor and it is usually in a range of 65° to 160° C. preferably 70° to 150° C. When the reaction temperature is 65° C. or lower, the production of 1,1,2-trichloroethane is remarkably small and it is unnecessary to add any side reaction inhibitor. When the reaction temperature is 160° C. or higher, the production of 1,1,2-trichloroethane is remarkable and an amount of the required side reaction inhibitor is large to be uneconomical.

In the high temperature process for reacting them at 65° to 160° C. to boil the upper liquid surface layer of the reaction medium, as the present invention, the reaction zone can be effectively cooled by the latent heat resulted in the evaporation of the reaction medium to advantageously eliminate a special means for cooling the reaction zone. In such high temperature process, the reaction heat can utilize as the heat source for the rectification to be remarkably advantageous in an industrial operation, by feeding a whole or part of vapor of 1,2-dichloroethane as the reaction product at the tower top, into the tower for the rectification of 1,2-dichloroethane.

The metal chloride catalyst incorporated in the reaction medium in the present invention can be a known metal chloride catalyst used in the reaction and can be ferric chloride, aluminum chloride, antimony chloride and copper chloride etc. The preferable metal chloride catalyst is ferric chloride.

An amount of the metal chloride catalyst is usually in a range of 10 to 6,000 ppm (by weight) preferably 30–2,000 ppm (by weight) as a concentration of the catalyst in the liquid phase of the reaction zone. When the body of the vessel of the reactor etc. is made of carbon steel, ferric chloride is naturally eluted to easily give the concentration of the catalyst whereby it is not necessary to feed a metal chloride as the catalyst. Higher concentration of the catalyst is not preferable because a trouble such as a clogging of an apparatus caused by a precipitation of the metal chloride is caused.

In the present invention, at least one of aromatic compounds selected from the group consisting of benzene type hydrocarbons having the formula

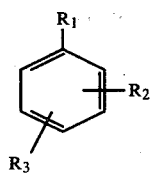

wherein $R_1$, $R_2$ and $R_3$ respectively represent hydrogen atom, a $C_1$–$C_5$ alkyl group, and chlorinated derivatives thereof as the side reaction inhibitor is incorporated in the liquid phase of the reaction zone. This is the most significant characteristic of the present invention. The production of 1,1,2-trichloroethane can be effectively reduced by incorporating the effective amount of the side reaction inhibitor even though the reaction condition is at high temperature for boiling 1,2-dichloroethane as the reaction medium. Thus, the industrial operation of the high temperature process which has said advantages can be attained as significant effect.

The compounds used in the present invention can be benzene type hydrocarbons such as benzene, toluene, xylene, ethylbenzene, ethyltoluene, mesitylene, n-butylbenzene, and cumene; and chlorinated derivatives of the benzene type hydrocarbons such as monochlorobenzene, dichlorobenzene, trichlorobenzene and chlorotoluene. The aromatic compound can be used by itself or a mixture thereof.

When benzene is used as the side reaction inhibitor and is fed into the reactor, benzene is converted into monochlorobenzene at first and is further sequentially converted into dichlorobenzene, trichlorobenzene, tetrachlorobenzene and pentachlorobenzene. Therefore, when the reaction is carried out by gradually feeding benzene, various chlorinated benzenes are remained in the liquid phase of the reaction zone instead of benzene to impart the effect for reducing the side reaction as benzene. Thus, the side reaction inhibitor fed into the reactor is not limited to benzene and one or more of chlorinated benzenes can be fed.

When toluene is used as the side reaction inhibitor, toluene is converted into monochlorotoluene at first in the reactor as the reaction of benzene and it is further sequentially converted into dichlorotoluene, trichlorotoluene, tetrachlorotoluene and pentachlorotoluene. The chlorinated toluenes also impart the effect for reducing the side reaction.

An economical compound is preferably used as the aromatic compound in an industrial process. The use of benzene is optimum.

An amount of the aromatic compound incorporated in the present invention is usually 0.001 wt.% or more preferably 0.01–20 wt.% especially 0.01 to 5 wt.% based on the liquid phase of the reaction zone. When the amount of the side reaction inhibitor is not enough, the production of 1,1,2-trichloroethane is large to be lower conversion to produce 1,2-dichloroethane. The production of 1,1,2-trichloroethane can be easily lowered to be 1.5 wt.% or less based on the resulting 1,2-dichloroethane and the selectivity to 1,2-dichloroethane can be 98.5% or higher by incorporating a required amount of the side reaction inhibitor. When the amount of the side reaction inhibitor is less than 0.001 wt.%, the production of 1,1,2-trichloroethane may be about 3 wt.% and the selectivity to 1,2-dichloroethane is lowered to about 97% or less. The feeding of the side reaction inhibitor into the reaction zone can be the feeding of the compound itself or after a dilution with a solvent such as 1,2-dichloroethane. When the side reaction inhibitor is used by diluting it with 1,2-dichloroethane, it is preferable to use 1,2-dichloroethane which does not contain an impurity for inhibiting the reaction of ethylene with chlorine.

When 1,2-dichloroethane which contains a large amount of an impurity for inhibiting the reaction, is used for diluting the side reaction inhibitor to use the side reaction inhibitor at a low concentration, the reaction of ethylene with chlorine is inhibited to reduce the selectivity to 1,2-dichloroethane and to reduce the yield.

The side reaction in the reaction for producing 1,2-dichloroethane from ethylene and chlorine is mainly the reaction for producing 1,1,2-trichloroethylene. Therefore, if the reaction for producing 1,1,2-trichloroethane can be reduced, the selectivity to 1,2-dichloroethane is increased.

PREFERRED EMBODIMENT OF THE INVENTION

Figure 1:
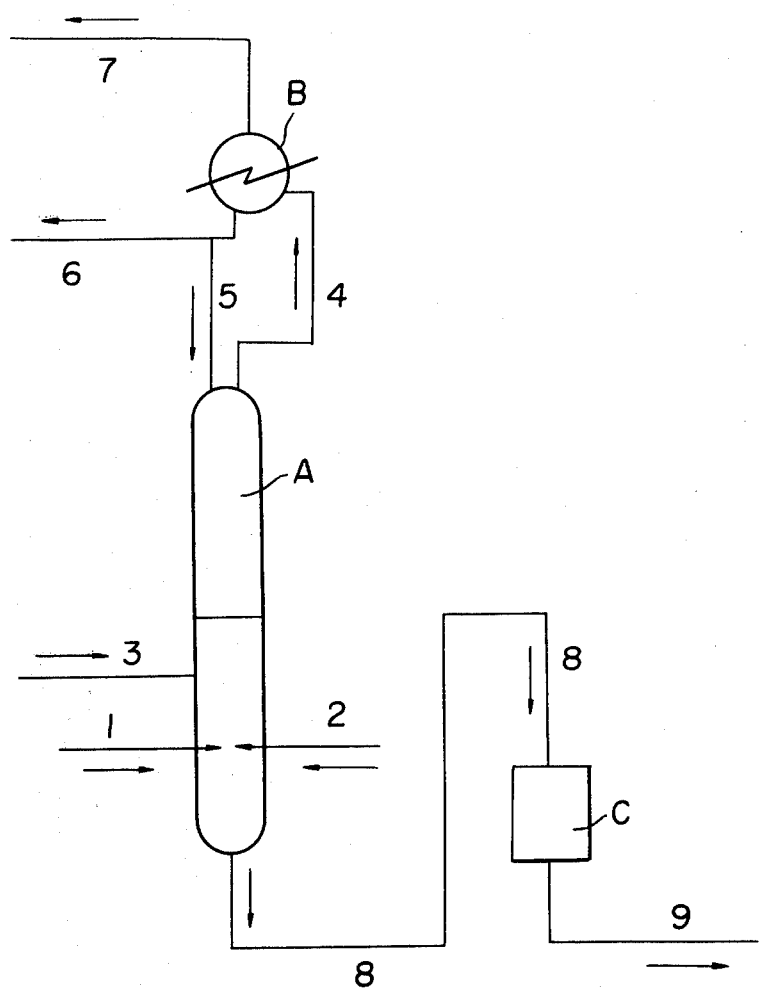
FIG. 1 is a schematic view of an apparatus for producing 1,2-dichloroethane used in the following example of the present invention; wherein (A) designates a reactor which comprises a chlorine gas inlet pipe (1), an ethylene inlet pipe (2) and a side reaction inhibitor inlet pipe (3) and (B) designates a condenser which cools and condenses a top vapor discharged from the top of the reactor (A) by a pipe (4) and the condensed liquid can be recycled through a pipe (5) into the reactor (A) or can be discharged through a pipe (6) outside and a pipe (7) is used for discharging noncondensed gas from the condenser (B); (C) designates a receiver and a bottom of the reactor (A) overflown through a pipe (8) is kept in the receiver (C) and is discharged through a pipe (9) outside.

The embodiment for producing 1,2-dichloroethane by using the apparatus shown in FIG. 1 will be illustrated.

In the reactor (A), 1,2-dichloroethane is charged as a reaction medium and a predetermined amount of a metal chloride catalyst is incorporated in the reaction medium. As described above, if the reactor (A) is made of a carbon steel, ferric chloride is naturally eluted during the reaction for producing 1,2-dichloroethane, whereby it is unnecessary to feed separately a metal chloride catalyst. Into the reaction medium in the reactor (A), chlorine gas and ethylene are respectively fed through the chlorine gas inlet pipe (1) and the ethylene inlet pipe (2) at each predetermined flow rate. The side reaction inhibitor such as benzene is fed at a predetermined flow rate through the side reaction inhibitor inlet pipe (3). Thus, the reaction of ethylene with chlorine is performed to produce 1,2-dichloroethane and 1,2-dichloroethane as the reaction medium and the reaction product is boiled to generate the vapor by the reaction heat.

In accordance with one embodiment, the top vapor of the reactor (A) (mainly 1,2-dichloroethane) is passed through the pipe (4) and is cooled and condensed in the condenser (B). A part of the condensed liquid is recycled through the pipe (5) to the reactor (A) and the remained part of the condensed liquid is discharged through the pipe (6) as a crude 1,2-dichloroethane. The gas which is not condensed in the condenser (B) is discharged through the pipe (7) as a waste gas.

In accordance with the other embodiment, the reaction heat of the reactor (A) is effectively utilized for the distillation of 1,2-dichloroethane as the product by feeding whole or most part of the vapor into a distillation tower for purification of 1,2-dichloroethane in the form of vapor without condensing the top vapor of the reactor (A) in a condenser or with condensing only small amount the vapor required for the recycling such as a liquid level control in the reactor (A). (This embodiment is optimum in an industrial process.)

In accordance with the other embodiment, all of the top vapor is condensed except the non-condensable gas, and all of the condensed liquid is recycled through the pipe (5) into the reactor (A). In this case, 1,2-dichloroethane as the reaction product is discharged from the bottom as overflowed liquid through the pipe (8), the receiver (C) and the pipe (9). The bottom overflowed liquid of the reactor (A) has substantially the same formulation as that of the liquid in the reaction zone. Therefore, it is convenient to test the formulation of the liquid phase in the reaction zone (for example, a content of the side reaction inhibitor). Thus, a part of the example of the specification is the example of this embodiment.

It is possible to equip a different cooling means (not shown) with the reactor (A) whereby the temperature at the lower part of the reactor (A) can be controlled.

In the embodiment of condensing whole of the top vapor of the reactor (A) to recycle it and discharging 1,2-dichloroethane as the reaction product as the overflowed liquid at the bottom of the reactor (A), a small amount of by-products such as 1,1,2-trichloroethane is discharged together with 1,2-dichloroethane whereby the by-products are not accumulated in the reaction zone.

In the embodiment of discharging 1,2-dichloroethane as the reaction product as the condensed liquid of the condenser (B) through the pipe (6), or the embodiment of discharging the top vapor of the reactor (A) in the form of vapor into the rectification tower, 1,1,2-trichloroethane (b.p. 113° C.) produced at a small ratio in the reaction zone is gradually accumulated in the reaction medium. Therefore, it is necessary to intermittently or continuously discharge the reaction medium in the form of liquid from the reactor (A) so as to prevent the accumulation. In such case, it is necessary to intermittently or continuously add the aromatic compound as the side reaction inhibitor in the liquid phase of the reaction zone so as to maintain the predetermined content of the side reaction inhibitor.

The present invention will be further illustrated by examples and references.

EXAMPLE 1

Into the reactor (A) made of a carbon steel having a diameter of 250 mm and a height of 10 m shown in FIG. 1, 1 2-dichloroethane was charged in a level of 4 m and chlorine gas and ethylene were respectively continuously fed through the inlet pipe (1) and the inlet pipe (2) at each flow rate of 20 Nm$^3$/hr. and benzene as the side reaction inhibitor was continuously fed through the inlet pipe (3) by a quantitative pump at a flow rate of 85 g./hr. to perform the continuous reaction. In the reaction medium, ferric chloride was eluted from the wall of the reactor to contain 50 to 200 ppm (by weight) of ferric chloride.

During the continuous reaction, the pressure in the reactor (A) was maintained to be 1.3 kg/cm$^2$G as the pressure at the position near the ethylene gas inlet port and a temperature in the reactor was maintained at 100° to 110° C. in the liquid phase. Therefore, 1,2-dichloroethane as the reaction medium in the reaction zone was boiled. The vapor was passed through the pipe (4) to the condenser (B) in which the vapor was cooled and condensed and all of the condensed liquid (60° C.) was recycled through the pipe (5) to the top of the reactor (A). The noncondensed gas in the condenser (B) was discharged as the waste gas through the pipe (7). The liquid phase in the reaction zone of the reactor (A) was boiled by reaction heat as described above. The portion of the liquid increased by the reaction for producing 1,2-dichloroethane was passed from the bottom of the reactor (A) as the overflowed liquid through the pipe (8) into the receiver (C) and it was discharged from the receiver (C) through the pipe (9).

The formulation of the overflowed reaction mixture discharged from the receiver (C) is shown in the following table. The formulation was the same as the formulation of the boiled liquid phase in the reaction zone which was separately sampled from the reaction zone.

In the table, the selectivities of the products in the reaction are described. The selectivities are calculated by the base of ethylene with the consideration of noncondensed gas (hereinafter the same).

|  | Formulation of overflowed reaction mixture | Selectivity |
| --- | --- | --- |
| 1,2-dichloroethane | 99.22 wt. % | 99.39% |
| 1,1,2-trichloroethane | 0.47 wt. % | 0.34% |
| ethylchloride | 0.01 wt. % | 0.23% |
| chlorinated benzene (total of chlorinated benzenes) | 0.26 wt. % | — |
| benzene | 0.002 wt. % | — |
| others | 0.04 wt. % | 0.04% |

Thus, the selectivity to 1,2-dichloroethane in the continuous reaction was 99.39%.

REFERENCE 1

In accordance with the process of Example 1 except that benzene was not fed, the continuous reaction was carried out under the same condition. As a result, the overflowed liquid having the following formulation was discharged. The selectivity to 1,2-dichloroethane in the continuous reaction was 96.93%.

|  | Formulation of overflowed reaction mixture | Selectivity |
| --- | --- | --- |
| 1,2-dichloroethane | 96.16 wt. % | 96.93% |
| 1,1,2-trichloroethane | 3.71 wt. % | 2.78% |
| ethylchloride | 0.02 wt. % | 0.18% |
| others | 0.11 wt. % | 0.11% |

EXAMPLE 2

In accordance with the process of Example 1 except that each of the flow rates of chlorine gas and ethylene was changed to 46 Nm³/hr. and the flow rate of benzene was changed to 20 g./hr. the continuous reaction was carried out under the same condition. As a result, the reaction mixture having the following formulation was discharged as the overflowed liquid from the bottom of the reactor (A). In the reaction, the selectivity to 1,2-dichloroethane was 99.72%.

|  | Formulation of overflowed reaction mixture | Selectivity |
| --- | --- | --- |
| 1,2-dichloroethane | 99.71 wt. % | 99.72% |
| 1,1,2-trichloroethane | 0.22 wt. % | 0.16% |
| ethylchloride | 0.01 wt. % | 0.08% |
| chlorinated benzenes (total of chlorinated benzenes) | 0.02 wt. % | — |
| benzene | 0.4 (wt. ppm) | — |
| others | 0.04 wt. % | 0.04% |

REFERENCE 2

In accordance with the process of Example 2 except that benzene was not fed, the reaction was carried out under the same condition. As a result, the reaction mixture having the following formulation was discharged as the overflowed liquid from the bottom of the reactor (A). In the reaction, the selectivity to 1,2-dichloroethane was 97.81%.

|  | Formulation of overflowed liquid | Selectivity |
| --- | --- | --- |
| 1,2-dichloroethane | 97.15 wt. % | 97.81% |
| 1,1,2-trichloroethane | 2.80 wt. % | 2.09% |
| ethylchloride | 0.01 wt. % | 0.06% |
| others | 0.04 wt. % | 0.04% |

REFERENCE 3

A multi-pipe type external cooler was equipped with the reactor (A) to maintain a temperature of the liquid phase of the reaction zone to 61° C. under cooling by the external cooler and benzene was fed as the same as Example 1 or benzene was not fed, the continuous reaction was carried out under the condition. As a result, the reaction mixture having the following formulation was discharged as the overflowed liquid from the bottom of the reactor (A).

In the case of feeding of benzene, the selectivity to 1,2-dichloroethane was 99.77%. In the case of non feeding of benzene, the selectivity to 1,2-dichlorobenzene was 99.63%. Difference of the selectivities was small.

Feeding of benzene

|  | Formulation of overflowed liquid | Selectivity |
| --- | --- | --- |
| 1,2-dichloroethane | 99.62 wt. % | 99.77% |
| 1,1,2-trichloroethane | 0.18 wt. % | 0.13% |
| ethylchloride | 0.01 wt. % | 0.06% |
| chlorinated benzenes (total of chlorinated benzenes) | 0.12 wt. % | — |
| benzene | 0.03 wt. % | — |
| others | 0.04 wt. % | 0.04% |

Non-feeding of benzene

|  | Formulation of overflowed liquid | Selectivity |
| --- | --- | --- |
| 1,2-dichloroethane | 99.57 wt. % | 99.63% |
| 1,1,2-trichloroethane | 0.40 wt. % | 0.30% |
| ethylchloride | 0.01 wt. % | 0.05% |
| others | 0.02 wt. % | 0.02% |

EXAMPLE 3

In accordance with the process of Example 2 except that the flow rate of benzene was changed to 2 g./hr. the continuous reaction was carried out under the same condition. As a result, the reaction mixture having the following formulation was discharged as the overflowed liquid from the bottom of the reactor (A). In the reaction, the selectivity to 1,2-dichloroethane was 98.87%.

|  | Formulation of overflowed liquid | Selectivity |
| --- | --- | --- |
| 1,2-dichloroethane | 98.73 wt. % | 98.87% |
| 1,1,2-trichloroethane | 1.20 wt. % | 0.89% |
| chlorinated benzenes (total of chlorinated benzenes) | 0.0027 wt. % | — |

-continued

| | Formulation of overflowed liquid | Selectivity |
|---|---|---|
| benzene | 0.2 (wt. ppm) | — |
| ethylchloride | 0.02 wt. % | 0.19% |
| others | 0.05 wt. % | 0.05% |

REFERENCE 4

In accordance with the process of Example 2 except that the flow rate of benzene was changed to 0.5 g./hr., the continuous reaction was carried out under the same condition. As a result, the reaction mixture having the following formulation was discharged as the overflowed liquid from the bottom of the reactor (A). In the reaction, the selectivity to 1,2-dichloroethane was 98.21%.

| | Formulation of overflowed liquid | Selectivity |
|---|---|---|
| 1,2-dichloroethane | 97.88 wt. % | 98.21% |
| 1,1,2-trichloroethane | 2.03 wt. % | 1.52% |
| chlorinated benzenes (total of chlorinated benzenes) | 0.0007 wt. % | — |
| benzene | 0.05 (wt. ppm) | — |
| ethylchloride | 0.04 wt. % | 0.22% |
| others | 0.05 wt. % | 0.05% |

EXAMPLE 4

In accordance with the process of Example 2 except that the flow rate of benzene was changed to 40 g./hr. and the liquid obtained by the reaction was passed at a flow rate of 162 kg./hr. as a top condensed liquid (distillate) and was discharged at a flow rate of 41 kg./hr. as the bottom overflowed liquid, the continuous reaction was carried out under the condition. As a result, the reaction mixtures having the following formulations were discharged from the top and the bottom of the reactor (A). In the reaction, the selectivity to 1,2-dichloroethane was 99.74%.

| | Distillate from top | Overflowed liquid from bottom | Selectivity |
|---|---|---|---|
| 1,2-dichloroethane | 99.92 wt. % | 98.80 wt. % | 99.74% |
| 1,1,2-trichloroethane | 0.01 wt. % | 0.85 wt. % | 0.13% |
| chlorinated benzenes (total of chlorinated benzenes) | — | 0.31 wt. % | |
| benzene | — | 0.0007 wt. % | |
| ethylchloride | 0.02 wt. % | 0.01 wt. % | 0.08% |
| others | 0.05 wt. % | 0.03 wt. % | 0.05% |

EXAMPLE 5

In accordance with the process of Example 4 except that the flow rate of benzene was changed to 5 g./hr. and the flow rate of the distillate from the top was changed to 193 kg./hr. and the flow rate of the overflowed liquid from the bottom was changed to 10 kg./hr., the continuous reaction was carried out under the same condition. As a result, the reaction mixtures having the following formulations were discharged as the liquids discharged from the top and the bottom of the reactor (A). In the reaction, the selectivity to 1,2-dichloroethane was 99.76%.

| | Distillate from top | Overflowed liquid from bottom | Selectivity |
|---|---|---|---|
| 1,2-dichloroethane | 99.93 wt. % | 96.28 wt. % | 99.76% |
| 1,1,2-trichloroethane | 0.02 wt. % | 3.52 wt. % | 0.14% |
| chlorinated benzenes (total of chlorinated benzenes) | — | 0.18 wt. % | — |
| benzene | — | 0.0000 wt. % | — |
| ethylchloride | 0.01 wt. % | 0.00 wt. % | 0.06% |
| others | 0.04 wt. % | 0.02 wt. % | 0.04% |

EXAMPLE 6

In accordance with the process of Example 2 except that dichlorobenzene was used instead of benzene and a solution of 1,2-dichloroethane containing 0.5 wt.% of dichlorobenzene was fed at a rate of 10 kg./hr. (50 g./hr. as dichlorobenzene), the continuous reaction was carried out under the same condition of Example 2. As a result, the reaction mixture having the following formulation was discharged as the overflowed liquid from the bottom of the reaction (A). In the reaction, the selectivity to 1,2-dichloroethane was 99.54%.

| | Formulation of overflowed liquid | Selectivity |
|---|---|---|
| 1,2-dichloroethane | 99.51 wt. % | 99.55% |
| 1,1,2-trichloroethane | 0.41 wt. % | 0.32% |
| ethylchloride | 0.01 wt. % | 0.09% |
| others | 0.04 wt. % | 0.04% |
| chlorinated benzene | 0.03 wt. % | — |

EXAMPLE 7

In accordance with the process of Example 1 except that toluene was fed at a rate of 85 g./hr. instead of benzene, the continuous reaction was carried out under the same condition. As a result, the reaction mixture having the following formulation was discharged as the overflowed liquid from the bottom of the reactor (A). In the reaction, the selectivity to 1,2-dichloroethane was 99.18%.

| | Formulation of overflowed liquid | Selectivity |
|---|---|---|
| 1,2-dichloroethane | 99.01 wt. % | 99.18% |
| 1,1,2-trichloroethane | 0.65 wt. % | 0.48% |
| ethylchloride | 0.01 wt. % | 0.30% |
| others | 0.04 wt. % | 0.04% |
| chlorinated toluenes | 0.29 wt. % | — |

EXAMPLE 8

In accordance with the process of Example 1 except that xylene was fed at a rate of 85 g./hr. instead of benzene, the continuous reaction was carried out under the same condition. As a result, the reaction mixture having the following formulation was discharged as the overflowed liquid from the bottom of the reactor (A). In the reaction, the selectivity to 1,2-dichloroethane was 99.03%.

| | Formulation of overflowed liquid | Selectivity |
|---|---|---|
| 1,2-dichloroethane | 98.86 wt. % | 99.03% |
| 1,1,2-trichloroethane | 0.84 wt. % | 0.62% |
| ethylchloride | 0.01 wt. % | 0.31% |
| others | 0.04 wt. % | 0.04% |
| chlorinated xylenes | 0.25 wt. % | — |

INDUSTRIAL UTILITY

In accordance with the present invention, 1,2-dichloroethane can be produced in high yield under reducing the production of by-products. This is remarkably advantageous in an industrial process.

We claim:

1. A process for producing 1,2-dichloroethane which comprises reacting ethylene with chlorine by a liquid phase reaction at a reaction temperature of 65° to 160° C. in a reaction medium containing 1,2-dichloroethane as a main component in the presence of a metal chloride catalyst, wherein at least one aromatic compound selected from the group consisting of benzene type hydrocarbons having the formula

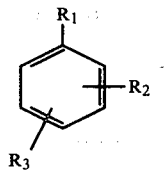

wherein $R_1$, $R_2$ and $R_3$ respectively represent hydrogen or $C_1$-$C_5$ alkyl and chlorinated derivatives thereof, as a side reaction inhibitor, is present in an amount of at least 0.001 wt.% based on the liquid phase in the liquid phase of the reaction zone.

2. The process according to claim 1 wherein said benzene type hydrocarbon or said chlorinated derivative thereof is benzene, toluene, xylene or a chlorinated derivative thereof.

3. The process according to claim 1 wherein said aromatic compound is present in an amount of 0.01 to 20 wt.% based on the liquid phase.

4. The process according to claim 1 wherein said metal chloride catalyst is ferric chloride and ferric chloride is present in an amount of 10 to 6,000 ppm in the reaction medium.

5. The process according to claim 1 wherein said reaction medium is boiled by reaction heat to discharge 1,2-dichloroethane in the form of vapor from the reaction zone and then it is condensed to obtain 1,2-dichloroethane.

6. The process according to claim 1 wherein said reaction medium is boiled by reaction heat to discharge 1,2-dichloroethane in the form of vapor from the reaction zone and then, it is condensed to obtain 1,2-dichloroethane and on the other hand, in order to prevent an accumulation of high boiling impurities in the reaction medium, a part of the reaction medium in the form of liquid is intermittently or continuously discharged from the reaction zone and the side reaction inhibitor is intermittently or continuously added to the reaction medium to maintain the predetermined content of the side reaction inhibitor.

* * * * *